United States Patent [19]

Reed et al.

[11] Patent Number: 5,604,215
[45] Date of Patent: Feb. 18, 1997

[54] STEROID SULPHATASE INHIBITORS

[75] Inventors: Michael J. Reed, London; Barry V. L. Potter, Bath, both of United Kingdom

[73] Assignee: Imperial College of Science, Technology and Medicine, England

[21] Appl. No.: 196,191

[22] PCT Filed: Aug. 28, 1992

[86] PCT No.: PCT/GB92/01586

§ 371 Date: Dec. 27, 1994

§ 102(e) Date: Dec. 27, 1994

[87] PCT Pub. No.: WO93/05063

PCT Pub. Date: Mar. 18, 1993

[30] Foreign Application Priority Data

Aug. 29, 1991 [GB] United Kingdom .................. 9118465

[51] Int. Cl.$^6$ .............................. C07J 31/00; C07J 51/00; A61K 31/565
[52] U.S. Cl. ............................ 514/178; 514/171; 552/626
[58] Field of Search ............................ 552/626; 514/178, 514/171

[56] References Cited

U.S. PATENT DOCUMENTS 4,150,126  4/1979  Fex et al. .

FOREIGN PATENT DOCUMENTS

| | | |
|---|---|---|
| 779841 | 6/1972 | Belgium . |
| 2069758 | 3/1971 | France . |
| 2133484 | 1/1972 | France . |
| 1949095 | 9/1970 | Germany . |
| 120016 | 5/1976 | Germany . |
| 201143 | 7/1983 | Germany . |
| 1398026 | 6/1975 | United Kingdom . |

OTHER PUBLICATIONS

Kimura et al, Chem. Pharm. Bull. 21(8) 1720–1726, 1973.
Schwarz et al, Pharmazie 30 pp. 17–21 1975.
Baldwin et al, J. Chem. Soc. (C) 2283–2289, 1968.
Riess et al, Bul. Soc. Chem. Fr., 4933–4941 1965.
Townsley et al, Res. Steroids, 5, 73–78, 1973.
Dibbelt et al, Z. Physiol. Chem. 365, S. 1145–1153, 1984.

Primary Examiner—Rebecca Cook
Attorney, Agent, or Firm—Nixon & Vanderhye

[57] ABSTRACT

Steroid sulphatase inhibitors and pharmaceutical compositions containing them for use in the treatment of oestrone dependent tumors, especially breast cancer. The steroid sulphatase inhibitors are sulphonate and phosphonate esters of formula (I)

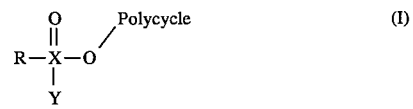

where R is alkyl, alkenyl, cycloalkyl or aryl; X is P or S; Y is OH when X is P, and O when X is S; and —O—polycycle represents the residue of a polycyclic alcohol such as a sterol, preferably a 3—sterol.

12 Claims, 2 Drawing Sheets

STEROID SULPHATASE INHIBITORS

This application is a 371 of PCT/6B92/01586 filed Aug. 28, 1992.

FIELD OF INVENTION

This invention relates to novel compounds for use as steroid sulphatase inhibitors, and pharmaceutical compositions containing them.

BACKGROUND AND PRIOR ART

Steroid precursors, or pro-hormones, having a sulphate group in the 3-position of the steroid nucleus, referred to hereinafter simply as steroid sulphates, are known to play an important part as intermediates in steroid metabolism in the human body. Oestrone sulphate and dehydroepiandrosterone (DHA) sulphate, for example, are known to play an important role as intermediates in the production, in the body, of oestrogens such as oestrone and oestradiol. Oestrone sulphate, in particular, is known, for example, to represent one of the major circulating oestrogen precursors particularly in post-menopausal women and oestrone sulphatase activity in breast tumours is 100–1000 fold greater than that of other enzymes involved in oestrogen formation (James et al., *Steroids*, 50, 269–279 (1987)).

Not only that, but oestrogens such as oestrone and oestradiol, particularly the over-production thereof, are strongly implicated in malignant conditions, such as breast cancer, see *Breast Cancer, Treatment and Prognosis*: Ed. R. A. Stoll, pp. 156–172, Blackwell Scientific Publications (1986), and the control of oestrogen production is the specific target of many anti-cancer therapies, both chemotherapy and surgical, e.g. oöphorectomy and adrenalectomy. So far as endocrine therapy is concerned, efforts have so far tended to concentrate on aromatase inhibitors, i.e. compounds which inhibit aromatase activity, which activity is involved, as the accompanying oestrogen metabolic flow diagram (FIG. 1) shows, in the conversion of androgens such as androstenedione and testosterone to oestrone and oestradiol respectively.

In recently published International Application WO91/13083 a proposal has been made to target a different point in the oestrogen metabolic pathway, or rather two different points, that is to say the conversion of DHA sulphate and oestrone sulphate to DHA and oestrone, respectively, by steroid sulphatase activity, and using 3-monoalkyl-thiophosphonate steroid esters as a steroid sulphatase inhibitor, more especially oestrone-3-monomethylthiophosphonate.

Also proposed as antitumour agents (see U.S. Pat. No. 4,150,126) are steroid enol esters of the Formula:

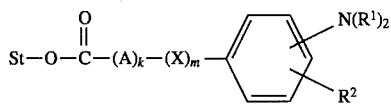

wherein:
$R^1$ is $(C_2-C_6)$ β- or γ-haloalkyl;
$R^2$ is H, lower alkyl, lower alkoxy or halogen;
A provides a $C_1-C_4$ hydrocarbon chain between

and X;
X is O or S;
k and m=0 or 1, with the proviso that when m=1 then k=1; and
St is a steroid skeleton to which the ester group is attached at the 3-position and adjacent a double bond in the steroid A ring.

However no mechanistic explanation is given of the antitumour activity of those compounds. In that disclosure brief mention is made that such steroid and esters can be prepared by transesterification inter alia of steroid-3-sulphonates of the Formula:

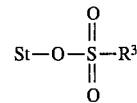

where St is a steroid nucleus as above defined, and $R^3$ is lower alkyl, optionally containing chloro- or fluoro-substituents, or phenyl, optionally substituted by chloro-, fluoro- or lower alkyl. However, no examples are given of any such steroid-3-sulphonates for use as intermediates in the preparation of the steroid enol esters described in that patent, let alone any suggestion that such steroid-3-sulphonates might themselves inhibit steroid sulphatase activity, and thus be of potential value in the treatment of oestrogen dependent tumours.

OBJECTS OF THE INVENTION

A first object of the present invention is to provide new compounds capable of inhibiting steroid sulphatase activity in vitro and in vivo.

A second object of the present invention is to provide new compounds having improved activity as steroid sulphatase inhibitors both in vitro and in vivo.

A third object of the invention is to provide pharmaceutical compositions effective in the treatment of oestrogen dependent tumours.

A fourth object of the invention is to provide pharmaceutical compositions effective in the treatment of breast cancer.

A fifth object of the invention is to provide a method for the treatment of oestrogen dependent tumours in mammals, especially humans.

A sixth object of the invention is to provide a method for the treatment of breast cancer in mammals and especially in women.

SUMMARY OF INVENTION

The invention is based on the discovery of novel compounds having steroid sulphatase inhibitory activity. These compounds are the sulphonate and phosphonate esters of polycyclic alcohols, being polycyclic alcohols the sulphate of which is a substrate for enzymes having steroid sulphatase activity.

Broadly speaking, the novel compounds of this invention are compounds of the Formula (I)

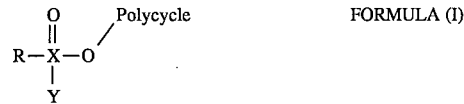
FORMULA (I)

where:
R is selected from H, alkyl, cycloalkyl, alkenyl and aryl;
X is P or S;
Y is —OH when X is P, and =O when X is S; and the group O-polycycle represents the residue of a polycyclic alcohol, the sulphate of which is a substrate for enzymes having steroid sulphatase activity, and their pharmaceutically acceptable salts.

As used herein the reference to polycyclic alcohols, the sulphate of which is a substrate for enzymes having steroid sulphatase activity refers to polycyclic alcohols, the sulphate of which is hydrolyzable by enzymes having steroid sulfatase (E.C. 3.1.6.1) activity, viz: the derivatives of the Formula:

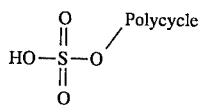

which when incubated with steroid sulphatase EC 3.1.6.2 at pH 7.4 and 37° C. and provides a Km value of less than 50 µmoles.

Figure 1:
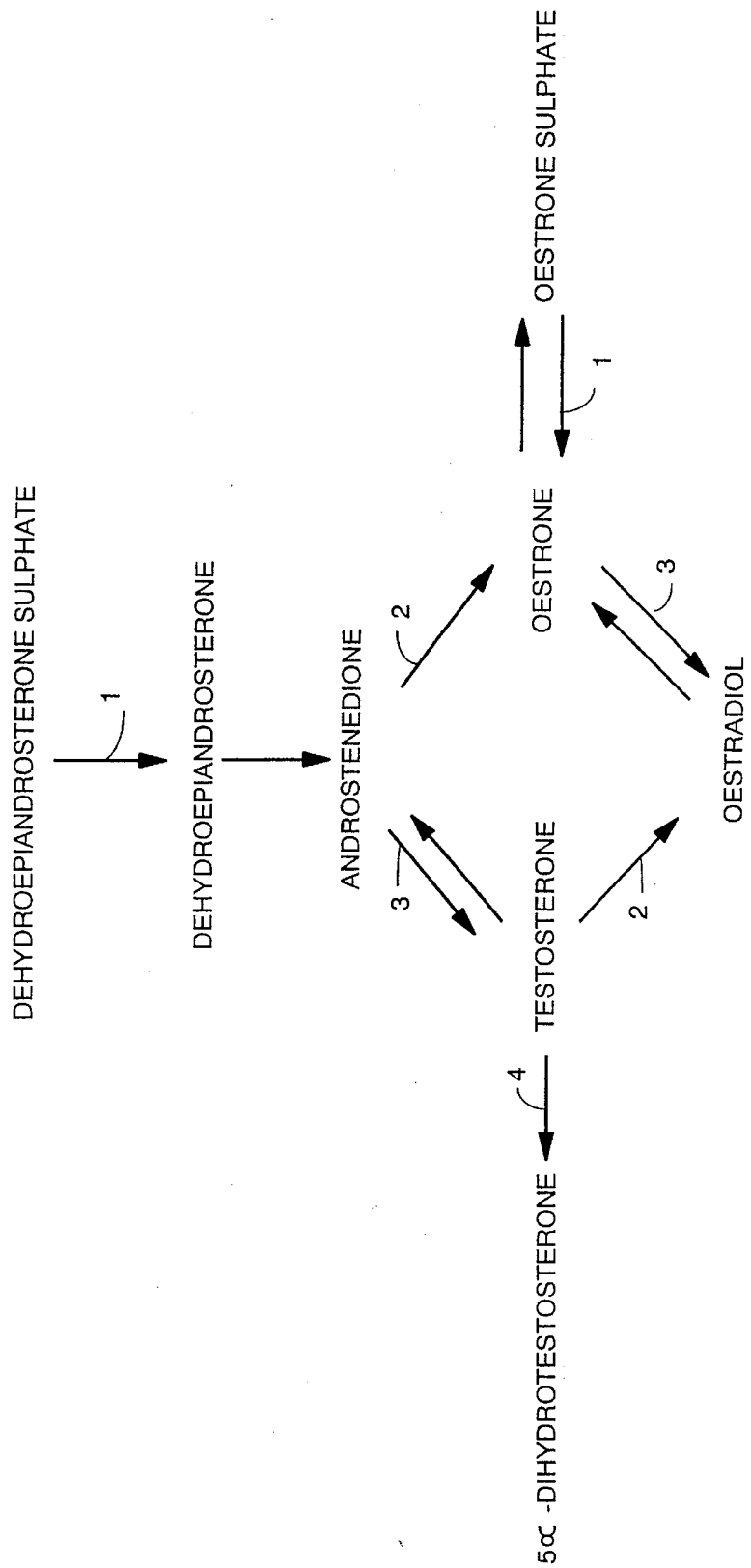
FIG. 1 is a schematic chart showing the metabolic pathways, enzymes and steroid intermediates associated with the production of oestradiol in vivo.
Figure 2:
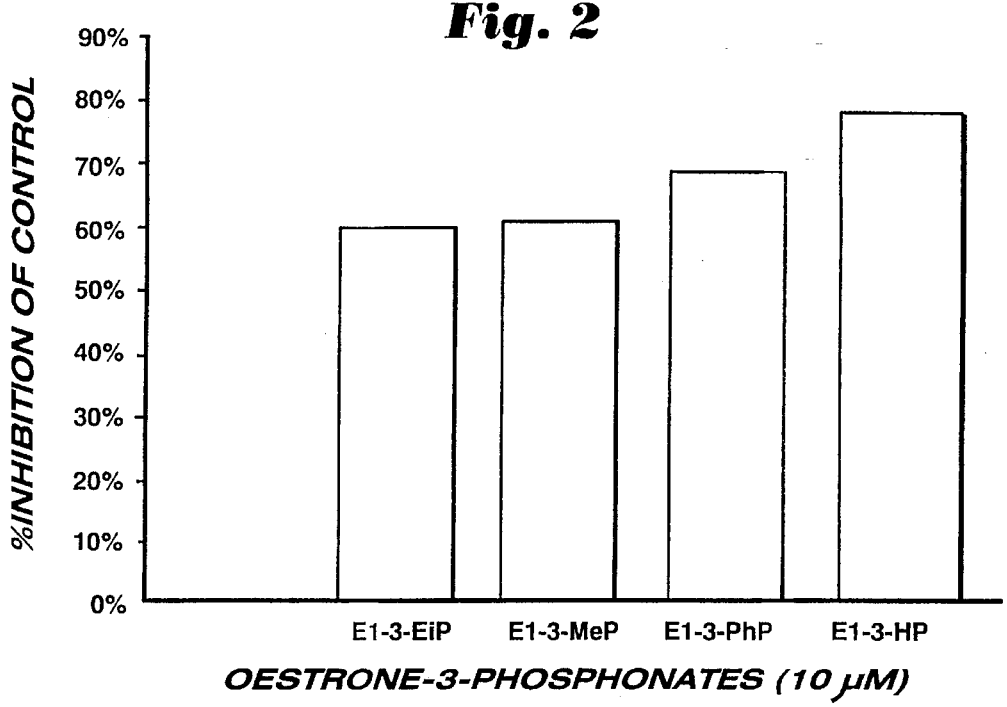

The activity of the present compounds as steroid sulphatase inhibitors is illustrated in the accompanying drawings:

FIG. 2 is a histogram showing the inhibitory effect of oestrone-3-phosphonates on steroid sulphatase activity in human MCF-7 cells in vitro.

Figure 3:
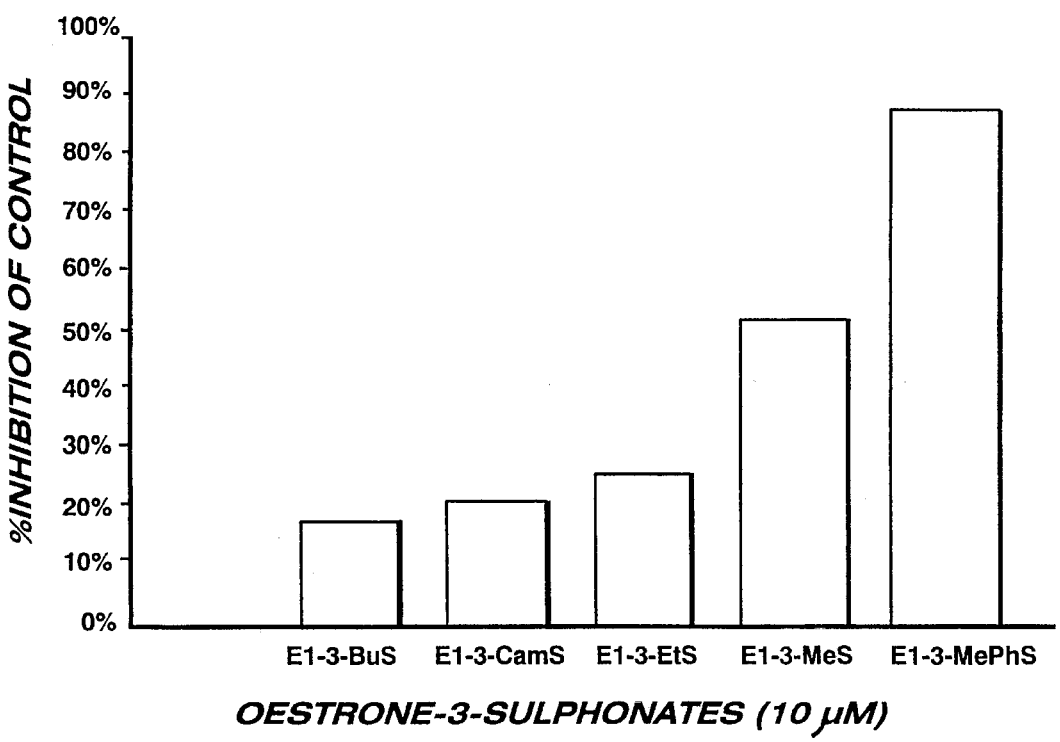

FIG. 3 is a histogram showing the inhibitory effect of oestrone-3-sulphonates on steroid sulphatase activity in human MCF-7 cells in vitro.

DETAILED DESCRIPTION

In one aspect the present invention provides, as novel compounds, the sulphonate and phosphonate acid esters of polycyclic alcohols, being polycyclic alcohols the sulphate of which is a substrate for enzymes having steroid sulphatase activity in accordance with the definition already provided. These compounds are of Formula I hereinbefore given.

Preferably the polycyclic group will contain, inclusive of all substituents, a maximum of about 40 carbon atoms, more usually no more than about 30. Preferred polycycles are those containing a steroidal ring structure, that is to say a cyclopentanophenanthrene skeleton. Preferably, the phosphonate or sulphonate group or substituted phosphonate or sulphonate group is attached to that skeleton in the 3-position, that is to say are compounds of Formula II.

FORMULA (II)

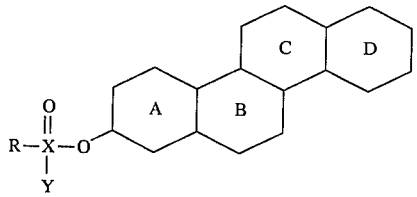

where R, X and Y are as above defined and the ring system ABCD represents a substituted or unsubstituted, saturated or unsaturated steroid nucleus, preferably oestrone or dehydroepiandrosterone.

Other suitable steroid ring systems are:
substituted oestrones, viz: 2-OH-oestrone,
2-methoxy-oestrone, 4-OH-oestrone, 6α-OH-oestrone,
7α-OH-oestrone, 16α-OH-oestrone, 16β-OH-oestrone
oestradiols and substituted oestradiols, viz: 2-OH-17β-oestradiol, 2-methoxy-17β-oestradiol, 4-OH-17β-oestradiol,
6α-OH-17β-oestradiol, 7α-OH-17β-oestradiol, 16α-OH-17α-oestradiol,
16β-OH-17α-oestradiol, 16β-OH-17β-oestradiol, 17α-oestradiol,
17β-oestradiol, 17α-ethinyl-17β-oestradiol
oestriols and substituted oestriols, viz: oestriol,
2-OH-oestriol, 2-methoxy-oestriol,
4-OH-oestriol, 6α-OH-oestriol, 7α-OH-oestriol
substituted dehydroepiandrosterones, viz: 6α-OH-dehydroepiandrosterone, 7α-OH-dehydroepiandrosterone,
16α-OH-dehydroepiandrosterone, 16β-OH-dehydroepiandrosterone In general terms the steroid ring system ABCD may contain a variety of non-interfering substituents. In particular, the ring system ABCD may contain one or more hydroxy, alkyl especially lower ($C_1$–$C_6$) alkyl, e.g. methyl, ethyl, n-propyl, isopropyl, n-butyl, sec-butyl, tert-butyl, n-pentyl and other pentyl isomers, and n-hexyl and other hexyl isomers, alkoxy especially lower ($C_1$–$C_6$) alkoxy, e.g. methoxy, ethoxy, propoxy etc., alkinyl, e.g. ethinyl, or halogen, e.g. fluoro substituents.

Other suitable non-steroidal ring systems include: diethylstilboestrol, stilboestrol and other such ring systems providing sulfates having $K_m$ values of less than 50 µmoles with steroid sulphatase EC3.1.6.2.

In the compounds of this invention, R preferably contains a maximum of 10 carbon atoms. When R is alkyl, the preferred values are lower alkyl groups containing from 1 to 5 carbon atoms, that is to say methyl, ethyl, propyl etc. Preferably R is H or methyl. When R is aryl, typical values are phenyl and tolyl (p-PhCH$_3$).

Within the values alkyl, cycloalkyl and aryl we include substituted alkyl, substituted cycloalkyl and substituted aryl, i.e. alkyl, cycloalkyl or aryl groups containing one or more substituent groups which do not interfere with the sulphatase inhibitory activity of the compound in question. Exemplary non-interfering substituents include hydroxy, carboxy, keto, amino, halo, alkoxy, alkyl and aryl. An example of a substituted cycloalkyl group suitable as R is camphoryl.

Also included within the scope of this invention are the pharmaceutically acceptable salts of those compounds, e.g. those where Y is OH, e.g. the non-toxic metal, ammonium and amine salts.

Most preferred are compounds of the Formula III and IV:

FORMULA (III)

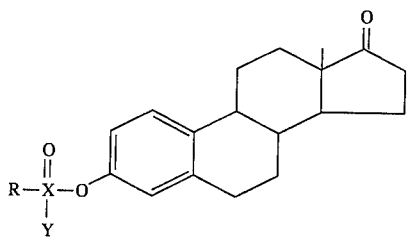

FORMULA (IV)

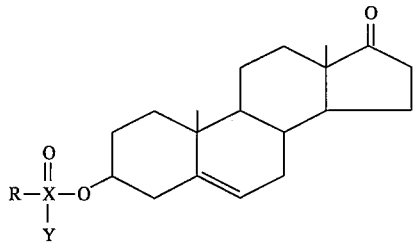

where R is H, $C_1$–$C_5$ alkyl, or aryl, e.g. phenyl or tolyl, i.e. oestrone-3-sulphonates and phosphonates and dehydroepiandrosteone-3-sulphonates and phosphonates, and especially the compounds where R is H, methyl, ethyl or phenyl, X is P and Y is —OH and the compounds where R is methyl, ethyl, phenyl or tolyl, X is S and Y is =O.

The compounds of this invention can be obtained by a variety of different reactions involving esterification of the corresponding polycyclic alcohol (sterol), possibly with one or more preliminary steps to introduce suitable protecting groups to protect other functional groups in the polycyclic alcohol, and which protective groups are removed at the end of the reaction.

In the case of the phosphonates there are, broadly speaking, two preparative routes, one which is appropriate for the synthesis phosphonates where R of Formula (II) is alkyl or aryl, employing a pentavalent phosphorus-containing reagent, such as alkyl or aryl phosphonic acid chloride or dichloride, e.g. reaction scheme 1:

REACTION SCHEME I

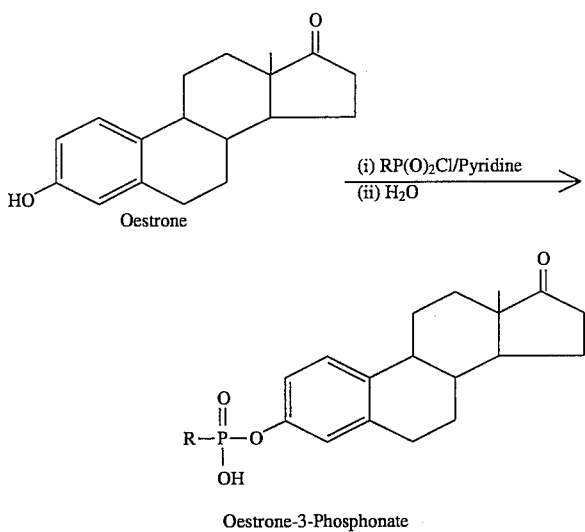

Oestrone-3-Phosphonate and the other, appropriate for the synthesis where R=H, employing a trivalent phosphorus reagent, e.g. the Reaction Scheme II.

REACTION SCHEME II

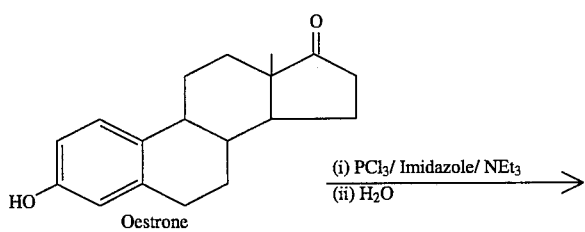

REACTION SCHEME II —continued

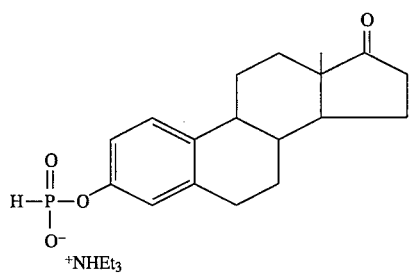

Triethylamine salt of
Oestrone-3-Hydrogen-Phosphonate

The sulphonates are obtained in analogous manner to reaction scheme I except that in this case the polycyclic alcohol (sterol) is reacted with an alkyl or aryl sulphonyl chloride $RSO_2Cl$ according to reaction scheme III below:

REACTION SCHEME III

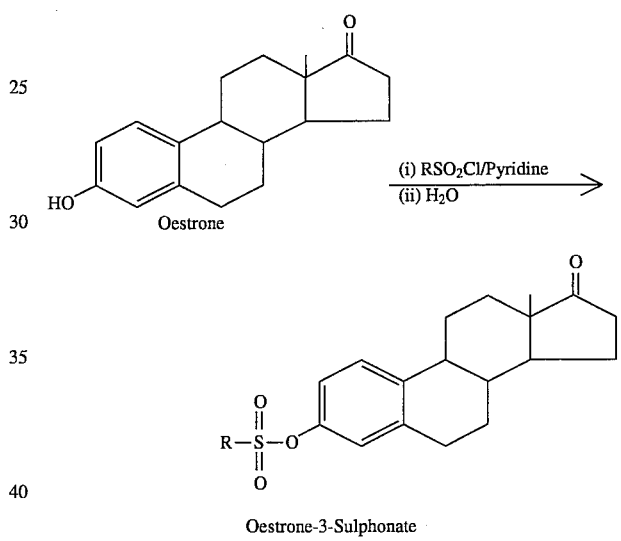

Oestrone-3-Sulphonate

Conditions for carrying out reaction scheme I are as follows:

A phosphonic dichloride is added dropwise to a stirred solution of oestrone in anhydrous pyridine at 0° C. Subsequently, the reaction is allowed to warm to room temperature and stirring is continued for a further 24 hours. The reaction mixture is poured onto ice and the resulting aqueous solution is extracted with ethyl acetate. The combined organic extracts are dried over anhydrous $MgSO_4$. Filtration followed solvent evaporation in vacuo and co-evaporation with toluene affords a crude gum. $K_2HPO_4$ buffer is added to this residue and the mixture is gently warmed to give a white, cloudy solution. The aqueous solution is washed with ethyl acetate and rendered acidic by adding a 2M(aq) solution of hydrochloric acid. On doing so, a solid precipitates out of solution and this is collected by suction filtration. The product is then dried and finally purified by recrystallisation.

Conditions for carrying out reaction scheme II are as follows:

Imidazole is dissolved in dry acetonitrile and cooled to 0° C. in an ice bath. Phosphorus trichloride is added to the solution and the mixture is stirred for 15 minutes. Triethylamine is added to the reaction and it is subsequently left to stir for a further 15 minutes. Finally a suspension of oestrone in dry acetonitrile is added and the reaction mixture is allowed to warm to room temperature and stirring is continued for another 20 hours. Distilled water is then carefully added to the reaction at 0° C. and the solution is left to stir at room temperature for 1 hour. Subsequently, the mixture is co-evaporated first with triethylamine and then with toluene to afford an oily residue which solidifies on standing. This residue is dissolved in chloroform and washed with water. The aqueous layer is then re-extracted with chloroform and the combined organic extracts are dried over anhydrous $MgSO_4$. Solvent evaporation in vacuo gives a white, glassy solid which is purified by flash chromatography to yield the desired compound as a colourless viscous oil.

Conditions for carrying out reaction scheme III are as follows:

A sulphonyl chloride is added dropwise to a stirred solution of oestrone in anhydrous pyridine at 0° C. Subsequently, the reaction is allowed to warm to room temperature and stirring is continued for a further 24 hours. The reaction mixture is poured onto ice and the resulting aqueous solution is extracted with ethyl acetate. The combined organic extracts are dried over anhydrous $MgSO_4$. Filtration followed by solvent evaporation in vacuo and co-evaporation with toluene affords a crude crystalline material, which is purified by recrystallisation.

Where necessary, functional groups in the polycyclic alcohol (sterol) may be protected in known manner and the protecting group or groups removed at the end of the reaction.

For pharmaceutical administration, the steroid sulphatase inhibitors of this invention can be formulated in any suitable manner utilising conventional pharmaceutical formulating techniques and pharmaceutical carriers, exipients, dilutents etc. and usually for parenteral administration. Approximate effective dose rates are in the range 100 to 800 mg/day depending on the individual activities of the compounds in question and for a patient of average (70 kg) bodyweight. More usual dosage rates for the preferred and more active compounds will be in the range 200 to 800 mg/day, more preferably, 200 to 500 mg/day, most preferably from 200 to 250 mg/day. They may be given in single dose regimes, split dose regimes and/or in multiple dose regimes lasting over several days. For oral administration they may be formulated in tablets, capsules, solution or suspension containing from 100 to 500 mg of compound per unit dose. Alternatively and preferably the compounds will be formulated for parenteral administration in a suitable parenterally administrable carrier and providing single daily dosage rates in the range 200 to 800 mg, preferably 200 to 500, more preferably 200 to 250 mg. Such effective daily doses will, however, vary depending on inherent activity of the active ingredient and on the bodyweight of the patient, such variations being within the skill and judgement of the physician.

For particular applications, it is envisaged that the steroid sulphatase inhibitors of this invention may be used in combination therapies, either with another sulphatase inhibitor, or, for example, in combination with an aromatase inhibitor, such as for example, 4-hydroxyandrostenedione (4-OHA).

The invention is illustrated by the following preparative Examples and test data.

EXAMPLE 1

Preparation of oestrone-3-hydrogenphosphonate

Imidazole (1.79 g; 26.34 mmols) was dissolved in dry acetonitrile (17 ml) and cooled to 0° C. in an ice bath. Phosphorus trichloride (0.60 ml; 7.95 mmols) was added to the solution and the mixture was stirred for 15 minutes. Triethylamine (3.88 ml; 27.84 mmols) was added to the reaction and it was subsequently left to stir for a further 15 minutes. Finally a suspension of oestrone (0.5 g; 1.85 mmols) in dry acetonitrile (17 ml) was added and the reaction mixture was allowed to warm to room temperature and stirring was continued for another 20 hours.

Distilled water (12.5 ml) was then carefully added to the reaction at 0° C. and the solution was left to stir at room temperature for an hour. Subsequently, the mixture was co-evaporated first with triethylamine (50 ml) and then with toluene (3×30 ml) to afford an oily residue which solidified on standing. This residue was dissolved in chloroform (20 ml) and washed with water (20 ml). The aqueous layer was then re-extracted with chloroform (3×20 ml) and the combined organic extracts were dried over anhydrous $MgSO_4$. Solvent evaporation in vacuo gave a white, glassy solid which was purified by flash chromatography (89:10:1, chloroform:methanol:triethylamine) to yield the desired compound as a colourless viscous oil (0.55 g; 68%). Analysis of the product was as follows:

Melting point: 208°–210° C.

$\delta^1H$ nmr (270 MHz; $CD_3OD$): 0.88 (s, 3H, $C_{18}$—Me), 1.29 (+, 9H, J=7.33 Hz, 3×—$CH_3$ of $NEt_3$), 1.30–2.60 (series of m, 15H), 3.14 (q, 6H, J=7.33 Hz, 3×—$CH_3$ of $NEt_3$), 6.88 (br d, 2H), 7.21 (br d, 1H).

$\delta^{13}C$ nmr (67.8 MHz; $CD_3OD$): 9.47 (q, —$NCH_2\underline{C}H_3$), 14.59 (q, $C_{18}$—Me), 22.74 (t), 27.24 (t), 27.76 (t), 30.68 (t), 33.02 (t), 36.98 (t), 39.83 (d), 45.51 (d), 47.78 (t, —N$\underline{C}H_2CH_3$), 51.73 (d), 79.85 (s, $C_{18}$), 119.43 (d), 122.30 (d), 127.70 (d), 136.60 (s), 139.37 (s), 152.00 (s), 223.45 (s, C=O). $\delta^{31}P$ nmr (109.37 MHz; $CD_3OD$) [$^1H$-decoupled]: 2.882 and −2.82 (d, J=630.4 Hz).

m/z $FAB^+$: 436 (M+H)$^+$ m/z $FAB^-$: 333 (M—$NEt_3$—H)$^-$

EXAMPLE 2

Preparation of oestrone-3-ethylphosphonate

Ethylphosphonyl dichloride (3 eq) was added dropwise to a stirred solution of oestrone (1 eq) in anhydrous pyridine at 0° C. Subsequently, the reaction was allowed to warm to room temperature and stirring was continued for a further 24 hours.

The reaction mixture was poured onto ice and the resulting aqueous solution was extracted with ethyl acetate. The combined organic extracts were dried over anhydrous $MgSO_4$. Filtration followed solvent evaporation in vacuo and co-evaporation with toluene afforded a crude gum.

$K_2HPO_4$ buffer (0.25M; pH 8.69) was added to this residue and the mixture was gently warmed to give a white, cloudy solution. The aqueous solution was washed with ethyl acetate and rendered acidic (pH 2) by adding a 2M(aq) solution of hydrochloric acid. On doing so, a solid precipitated out of solution and this was collected by suction filtration. The product was then dried and finally purified by recrystallisation. Analysis of the product was as follows:

Melting point: 208°–210° C.

$\delta^1H$ nmr (270 MHz; $CDCl_3$): 0.89 (s, 3H, $C_{18}$—Me), 1.00–2.60 (series of m, 18H), 2.86 (m, 2H), 6.90 (m, 2H), 7.19 (d, 1H, J=8.43 Hz), 9.73 (br s, exchangeable, 1H, —OH).

$\delta^{13}C$ nmr (67.8 MHz; $CDCl_3$): 6.21 (q, —$Ph_2CH_3$), 13.80 (q, $C_{18}$—Me), 17.76 and 19.88 (dt, J=144.30 Hz, —$Ph_2\underline{C}H_3$), 21.55 (t), 25.75 (t), 26.34 (t), 29.35 (t), 31.54 (t), 35.81 (t), 38.05 (d), 44.05 (d), 47.91 (s, $C_{18}$), 50.42 (d), 117.93 (d), 120.67 (d), 126.48 (d), 136.36 (s), 138.16 (s), 148.04 (s), 220.66 (s, C=O).

$\delta^{31}P$ nmr (109.37 MHz; $CDCl_3$) [$^1H$-decoupled]: 33.71.

m/z $FAB^+$: 363.1 (M+H)$^+$ m/z FAB⁻: 361.1 (M—H)⁻

Microanalysis:

|  | C | H | N |
|---|---|---|---|
| Expected: | 63.90% | 7.64% | 0.0% |
| Found: | 63.70% | 7.35% | 0.0% |

EXAMPLE 3

Preparation of oestrone-3-methylsulphonate (oestrone-3-mesylate)

Methylsulphonyl chloride (2 eq) was added dropwise to a stirred solution of oestrone (1 eq) in anhydrous pyridine at 0° C. Subsequently, the reaction was allowed to warm to room temperature and stirring was continued for a further 24 hours.

The reaction mixture was poured onto ice and the resulting aqueous solution was extracted with ethyl acetate. The combined organic extracts were dried over anhydrous $MgSO_4$. Filtration followed solvent evaporation in vacuo and co-evaporation with toluene afforded a crude crystalline material, which was purified by recrystallisation. Analysis of the product was as follows:

Melting point: 152°–154° C.

$\delta^1H$ nmr (270 MHz; $CDCl_3$): 0.92 (s, 3H, $C_{18}$—Me), 1.40–1.75 (m, 5H), 2.00–2.60 (series of m, 6H), 2.95 (m, 2H), 3.14 (s, 3H, —$SO_2CH_3$), 7.03 (m, 2H), 7.30 (m, 1H).

$\delta^{13}C$ nmr (67.8 MHz; $CDCl_3$): 13.74 (q, $C_{18}$—Me), 21.50 (t), 25.66 (t), 26.11 (t), 29.32 (t), 31.43 (t), 35.76 (t), 37.23 (q, —$SO_2CH_3$), 37.80 (d), 44.05 (d), 47.83 (s, $C_{18}$), 50.31 (d), 118.94 (d), 121.94 (d), 126.87 (d), 138.81 (s), 139.11 (s), 147.09 (s), 220.53 (s, C=O).

m/z (%): 348 (100) (m⁺), 291 (23), 213 (29), 97 (26), 65 (46), 57 (51), 41 (53), 29 (23).

Microanalysis:

|  | C | H | N |
|---|---|---|---|
| Expected: | 65.49% | 6.94% | 0.0% |
| Found: | 65.20% | 6.98% | 0.0% |

EXAMPLE 4

Inhibition of Steroid Sulphatase Activity in MCF-7 cells by oestrone-3-phosphonates Steroid sulphatase is defined as: Steryl Sulphatase EC 3.1.6.2.

Steroid sulphatase activity was measured in vitro using intact MCF-7 human breast cancer cells. This hormone dependent cell line is widely used to study the control of human breast cancer cell growth. It possesses significant steroid sulphatase activity (MacIndoe et al. *Endocrinology*, 123, 1281–1287 (1988); Purohit & Reed, *Int. J. Cancer*, 50, 901–905 (1992)) and is available in the U.S.A. from the American Type Culture Collection (ATCC) and in the U.K. (e.g. from the Imperial Cancer Research Fund). Cells were maintained in Minimal Essential Medium (MEM) (Flow Laboratories, Irvine, Scotland) containing 20 mM HEPES, 5% foetal bovine serum, 2 mM glutamine, non-essential amino acids and 0.075% sodium bicarbonate. Up to 30 replicate 25 cm² tissue culture flasks were seeded with approximately $1\times10^5$ cells/flask using the above medium. Cells were grown to 80% confluency and medium was changed every third day.

Intact monolayers of MCF-7 cells in triplicate 25 cm² tissue culture flasks were washed with Earle's Balanced Salt Solution (EBSS from ICN Flow, High Wycombe, U.K.) and incubated for 3–4 hours at 37° C. with 5 pmol ($7\times10^5$ dpm) [6,7-³H]oestrone-3-sulphate (specific activity 60 Ci/mmol from New England Nuclear, Boston, Mass., U.S.A.) in serum-free MEM (2.5 ml) together with 10 μM of each of four oestrone-3-phosphonates:

|  | Abbreviation |
|---|---|
| oestrone-3-hydrogen-phosphonate | $E_1$-3-HP |
| oestrone-3-methylphosphonate | $E_1$-3-MeP |
| oestrone-3-ethylphosphonate | $E_1$-3-EtP |
| oestrone-3-phenylphosphonate | $E_1$-3-PhP |

After incubation each flask was cooled and the medium (1 ml) was pipetted into separate tubes containing [¹⁴C] oestrone ($7\times10^3$ dpm) (specific activity 97 Ci/mmol from Amersham International Radiochemical Centre, Amersham, U.K.). The mixture was shaken thoroughly for 30 seconds with toluene (5 ml). Experiments showed that >90% [¹⁴C] oestrone and <0.1% [³H]oestron-3-sulphate was removed from the aqueous phase by this treatment. A portion (2 ml) of the organic phase was removed, evaporated and the ³H and ¹⁴C content of the residue determined by scintillation spectrometry. The mass of oestrone-3-sulphate hydrolysed was calculated from the ³H counts obtained (corrected for the volumes of the medium and organic phase used, and for recovery of [¹⁴C]oestrone added) and the specific activity of the substrate. Each batch of experiments included incubations of microsomes prepared from a sulphatase-positive human placenta (positive control) and flasks without cells (to assess apparent non-enzymatic hydrolysis of the substrate). The number of cell nuclei per flask was determined using a Coulter Counter after treating the cell monolayers with Zaponin. One flask in each batch was used to assess cell membrane status and viability using the Trypan Blue exclusion method (Phillips, H. J. (1973) In: *Tissue culture and applications*. [eds: Kruse, D. F. & Patterson, M. K. ]; pp. 406–408; Academic Press, New York).

Results for oestrone-3-phosphonates are shown in Table I and FIG. 2. Results are expressed as the mean ±1 S.D. of the total product (oestrone+oestradiol) formed during the incubation period (20 hours) calculated for 10⁶ cells and as a percentage reduction (inhibition) over incubations containing no oestrone-3-phosphonate for values showing statistical significance. Unpaired Student's t-test was used to test the statistical significance of results.

TABLE I

Steroid Sulphatase Activity in MCF-7 cells in the presence of Oestrone-3-phosphonates

| Oestrone-3-phosphonate | Concentration | Steroid Sulphatase Activity (fmol/20 hr/10⁶ cells) | % reduction over control (% inhibition) |
|---|---|---|---|
| (control) | 0 | ¶46.5 ± 2.3 | — |
| $E_1$-3-MeP | 10 μM | ¶17.6 ± 1.7*** | 62.2% |
| $E_1$-3-EtP | 10 μM | ¶18.4 ± 2.8*** | 60.4% |
| $E_1$-3-PhP | 10 μM | ¶13.8 ± 0.7*** | 70.3% |
| (Control) | 0 | §71.3 | — |
| $E_1$-3-HP | 10 μM | §14.2 | 80.1% |

¶ mean ± 1 S.D. n = 3
§ mean of 2 estimates
***p ≤ 0.001

EXAMPLE 5

Inhibition of Steriod Sulphatase Activity in MCF-7 cells by oestrone-3-sulphonates An identical experimental protocol to that described in Example 4 was used to generate results for oestrone-3-sulphonates except that incubations contained, in place of oestrone-3-phosphonates, each of five oestrone-3-sulphonates:

|  | Abbreviation |
| --- | --- |
| oestrone-3-methylsulphonate | $E_1$-3-MeS |
| oestrone-3-ethylsulphonate | $E_1$-3-EtS |
| oestrone-3-n-butylsulphonate | $E_1$-3-BuS |
| oestrone-3-camphorylsulphonate | $E_1$-3-CamS |
| oestrone-3-p-toluenesulphonate | $E_1$-3-MePhS |

Results for oestrone-3-sulphonates are shown in Table II and FIG. 3 are expressed in an identical manner to Table I and FIG. 2 respectively.

TABLE II

Steroid Sulphatase Activity in MCF-7 cells in the presence of Oestrone-3-sulphonates

| Oestrone-3-sulphonate | Concentration | Steroid Sulphatase Activity (fmol/20 hr/$10^6$ cells) | % reduction over control (% inhibition) |
| --- | --- | --- | --- |
| (control) | 0 | ¶80.1 ± 3.3 | — |
| $E_1$-3-EtS | 10 μM | ¶58.4 ± 1.9** | 27.1% |
| $E_1$-3-BuS | 10 μM | ¶66.8 ± 3.3* | 16.6% |
| $E_1$-3-CamS | 10 μM | ¶62.7 ± 1.8** | 21.7% |
| (Control) | 0 | ¶46.5 ± 2.3 | — |
| $E_1$-3-MeS | 10 μM | ¶21.3 ± 3.5** | 54.2% |
| (Control) | 0 | §71.3 | — |
| $E_1$-3-MePhS | 10 μM | §6.8 | 90.5% |

¶ mean ± 1 S.D. n = 3
§ mean of 2 estimates
\*p ≦ 0.05
\*\*p ≦ 0.01

EXAMPLE 6

Inhibition of Steroid Sulphatase Activity in Placental Microsomes by oestrone-3-phosphonates Sulphatase-positive human placenta from normal term pregnancies (Obstetric Ward, St. Mary's Hospital, London) were thoroughly minced with scissors and washed once with cold phosphate buffer (pH 7.4, 50 mM) then re-suspended in cold phosphate buffer (5 ml/g tissue). Homogenisation was accomplished with an Ultra-Turrax homogeniser, using three 10 second bursts separated by 2 minute cooling periods in ice. Nuclei and cell debris were removed by centrifuging (4° C.) at 2000 g for 30 minutes and portions (2 ml) of the supernatent were stored at −20° C. The protein concentration of the supernatents was determined by the method of Bradford (*Anal. Biochem.*, 72, 248–254 (1976)).

Incubations (1 ml) were carried out using a protein concentration of 100 μg/ml, substrate concentration of 20 μM [6,7-$^3$H]oestrone-3-sulphate (specific activity 60 Ci/mmol from New England Nuclear, Boston, Mass., U.S.A.) and an incubation time of 20 minutes at 37° C. The following oestrone-3-phosphonates were added to separate samples at a range of concentrations individually adjusted to span the 50% inhibition level:

|  | Abbreviation |
| --- | --- |
| oestrone-3-hydrogen-phosphonate | $E_1$-3-HP |
| oestrone-3-methylphosphonate | $E_1$-3-MeP |
| oestrone-3-ethylphosphonate | $E_1$-3-EtP |
| oestrone-3-phenylphosphonate | $E_1$-3-PhP |

After incubation each sample was cooled and the medium (1 ml) was pipetted into separate tubes containing [$^{14}$C] oestrone (7×$10^3$ dpm) (specific activity 97 Ci/mmol from Amersham International Radiochemical Centre, Amersham, U.K.). The mixture was shaken thoroughly for 30 seconds with toluene (5 ml). Experiments showed that >90% [$^{14}$C] oestrone and <0.1% [$^3$H]oestrone-3-sulphate was removed from the aqueous phase by this treatment. A portion (2 ml) of the organic phase was removed, evaporated and the $^3$H and $^{14}$C content of the residue determined by scintillation spectrometry. The mass of oestrone-3-sulphate hydrolysed was calculated from the $^3$H counts obtained (corrected for the volumes of medium and organic phase used, and for recovery of [$^{14}$C]oestrone added) and the specific activity of substrate.

Results for steroid sulphatase activity are expressed in Table III as calculated $IC_{50}$ values (i.e. the concentration of oestrone-3-phosphonate which produced 50% inhibition in relation to control).

TABLE III

Steroid Sulphatase Activity in placental microsomes in the presence of Oestrone-3-phosphonates

| Oestrone-3-phosphonate | Steroid Sulphatase Activity ($IC_{50}$ mol/l) |
| --- | --- |
| $E_1$-3-HP | 5.0 × $10^{-3}$ |
| $E_1$-3-MeP | 8.5 × $10^{-3}$ |
| $E_1$-3-PhP | 9.4 × $10^{-3}$ |
| $E_1$-3-EtP | 9.5 × $10^{-3}$ |

EXAMPLE 7

Inhibition of Steroid Sulphatase Activity in Placental Microsomes by oestrone-3-sulphonates An identical experimental protocol to that described in Example 6 was used to generate results for oestrone-3-sulphonates except that incubations contained, in place of oestrone-3-phosphonates, two representative oestrone-3-sulphonates:

|  | Abbreviation |
| --- | --- |
| oestrone-3-methylsulphonate | $E_1$-3-MeS |
| oestrone-3-p-toluenesulphonate | $E_1$-3-MePhS |

Results for steroid sulphatase activity are expressed in Table IV as calculated $IC_{50}$ values (i.e. the concentration of oestrone-3-sulphonate which produced 50% inhibition in relation to controls.

TABLE IV

Steroid Sulphatase Activity in placental microsomes in the presence of Oestrone-3-sulphonates

| Oestrone-3-sulphonate | Steroid Sulphatase Activity ($IC_{50}$ mol/l) |
|---|---|
| $E_1$-3-MePhS | $1.30 \times 10^{-4}$ |
| $E_1$-3-MeS | $2.05 \times 10^{-4}$ |

EXAMPLE 8

The following compounds already referred to herein and shown to inhibit steroid sulphatase activity, Examples 4 to 7, were prepared by the general procedure of Example 2:

oestrone-3-tosylate (Oestrone-3-p-toluenesulphonate
Analytical data:
$\delta^1$H nmr (270 MHz; $CDCl_3$): 0.91 (s, 3H, $C_{18}$—Me), 1.40–1.80 (m, 6H), 1.80–2.60 (series of m, 7H), 2.46 (s, 3H, Me—$C_3H_6$), 2.84 (m, 2H), 6.75 (dm, 2H), 7.20 (m, 1H), 7.35 (d, 2H, J=8.24 Hz), 7.78 (d, 2H, J=8.06 Hz).

m/z $FAB^+$: 424 (M+)
Microanalysis:

|  | C | H | N |
|---|---|---|---|
| Expected: | 70.90% | 6.65% | 0.0% |
| Found: | 70.80% | 6.77% | 0.0% | oestrone-3-phenylphosphonate
Analytical data:
$\delta^1$H nmr (270 MHz; $CDCl_3$): 0.88 (s, 3H, $C_{18}$—Me), 1.47 (m, 6H), 1.90–2.60 (series of m, 7H), 2.78 (br d, 2H), 6.86 (d, 2H, J=8.06 Hz), 7.43–7.87 (series of m, 5H), 9.62 (broad s, 1H, —OH).

$\delta^{31}$P nmr (109.37 MHz; $CDCl_3$) [$^1$H-decoupled]; 17.16.
m/z $FAB^+$: 411 (M+H)$^+$
m/z $FAB^-$: 409 (M—H)$^-$
Microanalysis: In accord with $C_{24}H_{27}O_6P\cdot\frac{1}{2}H_2O$

|  | C | H | N |
|---|---|---|---|
| Expected: | 68.72% | 6.73% | 0.0% |
| Found: | 68.70% | 6.54% | 0.0% | oestrone-3-methylphosphonate
Analytical data:
$\delta^1$H nmr (270 MHz; $(CD_3)_2SO$): 0.84 (s, 3H, $C_{18}$—Me), 1.35–2.50 (series of m, 13H), 1.44 (d, 3H, J=17.22 Hz, P—Me), 2.84 (m, 2H), 6.91 (br d, 2H, J=12.82 Hz), 7.26 (br d, 1H, J=8.25 Hz).

$\delta^{31}$P nmr (109.37 MHz; $(CD_3)_2SO$) [$^1$H-decoupled]: 24.47.
m/z $FAB^+$: 349 (M+H)$^+$
m/z $FAB^-$: 347 (M—H)$^-$
Microanalysis:

|  | C | H | N |
|---|---|---|---|
| Expected: | 65.50% | 7.23% | 0.0% |
| Found | 65.10% | 7.17% | 0.1% |

We claim:
1. A pharmaceutical composition comprising in admixture with a pharmaceutically acceptable diluent or carrier a compound of the formula

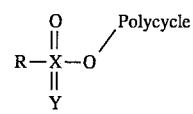

where
R is H or alkenyl;
X is S;
Y is O;
the group —O— polycycle represents the residue of a sterol;
the sulfate of which is hydrolyzable by an enzyme having steroid sulphatase (E.C. 3.1.6.2)activity; or a pharmaceutically acceptable salt thereof.

2. The composition according to claim 1, wherein R is hydrogen.

3. The composition according to claim 1 wherein the sterol is a 3-sterol.

4. The composition according to claim 3, wherein the sterol is selected from the group consisting of oestrone, dehydroepiandrosterone, a substituted oestrone and a substituted dehydroepiandrosterone.

5. The composition according to claim 1, wherein the compound is oestrone-3-sulphonate.

6. The composition according to claim 1 wherein said sterol is an oestradiol or substituted oestradiol.

7. The composition according to claim 1 wherein said sterol is an oestriol or substituted oestriol.

8. A method of treating a sensitive oestrogen dependent tumor comprising administering to a mammal an effective amount of a compound of the formula

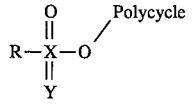

where
R is H or alkenyl;
X is S;
Y is O;
the group —O— polycycle represents the residue of a sterol; the sulfate of which is hydrolyzable by an enzyme having steroid sulphatase (E.C.3.1.6.2) activity; or a pharmaceutically acceptable salt thereof.

9. The method according to claim 8, wherein R, is hydrogen.

10. The method according to claim 8, wherein the sterol is a 3-sterol.

11. The method according to claim 8, wherein the sterol is selected from the group consisting of oestrone, dehydroepiandrosterone, a substituted oestrone and a substituted dehydroepiandrosterone.

12. The method according to claim 8, wherein the compound is oestrone-3-sulphonate.

\* \* \* \* \*